(12) United States Patent
Bodor et al.

(10) Patent No.: US 8,801,714 B1
(45) Date of Patent: Aug. 12, 2014

(54) SURGICAL RONGEUR

(75) Inventors: Peter Pal Bodor, Pembroke Pines, FL (US); Shusheng Ye, Davie, FL (US)

(73) Assignee: Vikon Surgical, LLC, Birmingham, AL (US)

( * ) Notice: Subject to any disclaimer, the term of this patent is extended or adjusted under 35 U.S.C. 154(b) by 664 days.

(21) Appl. No.: 13/083,742

(22) Filed: Apr. 11, 2011

Related U.S. Application Data

(60) Provisional application No. 61/438,754, filed on Feb. 2, 2011.

(51) Int. Cl.
*A61B 17/16* (2006.01)

(52) U.S. Cl.
USPC .............................. 606/83; 606/167; 600/564

(58) Field of Classification Search
USPC .......... 600/562, 564, 567; 606/79, 83, 84, 90, 606/99, 110, 167, 168, 170, 172, 174, 184, 606/205–210, 246, 114; 30/113.1, 113.2, 30/113.3; 227/175.1, 41, 42, 72, 75, 76, 227/128
See application file for complete search history.

(56) References Cited

U.S. PATENT DOCUMENTS

| | | | | |
|---|---|---|---|---|
| 4,491,261 | A * | 1/1985 | Mitsuhashi | 227/76 |
| 5,476,101 | A * | 12/1995 | Schramm et al. | 600/567 |
| 5,569,258 | A * | 10/1996 | Gambale | 606/83 |
| 5,961,531 | A * | 10/1999 | Weber et al. | 606/167 |
| 8,206,408 | B2 * | 6/2012 | Rebstock et al. | 606/167 |
| 8,556,899 | B2 * | 10/2013 | Heinemann | 606/83 |

* cited by examiner

*Primary Examiner* — Todd Manahan
*Assistant Examiner* — Marcela I Shirsat
(74) *Attorney, Agent, or Firm* — C. Brandon Browning; Maynard, Cooper & Gale, PC

(57) ABSTRACT

A rongeur including a stationary shaft having a length that terminates in a foot plate, a cutting slide slideably coupled with the stationary shaft and terminating in a cutting edge, a breach extending between the foot plate and the cutting edge for receiving human tissue, and handle means for slidably moving the cutting slide longitudinally relative to the shaft member. The cutting slide is provided with a pair of opposing tracking arms arranged about a distal end of the cutting slide and a third tracking arm arranged about the proximal end of the cutting slide. The tracking arms are slidably and detachably received within corresponding tracking slots in the shaft member when the rongeur is in a closed position. The tracking arms are disengaged from the tracking slots by rotating the cutting slide about a pivot axis that extends substantially parallel to the length of the shaft member thereby placing the rongeur in an open position.

22 Claims, 11 Drawing Sheets

SURGICAL RONGEUR

CROSS-REFERENCES TO RELATED APPLICATIONS

This application is a continuation of and claims priority to U.S. provisional application Ser. No. 61/438,754 filed on Feb. 2, 2011, the disclosure of which is incorporated herein by reference in its entirety for any and all purposes.

FIELD OF THE INVENTION

This invention relates generally to surgical rongeurs, and more particularly to Kerrison-style rongeurs used in laminectomies and laminotomies.

BACKGROUND OF THE INVENTION

Kerrison rongeurs are utilized in spinal surgery to remove bone and tissue and thereby gain access to the spinal canal. Kerrison rongeurs typically comprise a stationary shaft and a cutting slide that is longitudinally slidable relative to the stationary shaft. At the distal end of the cutting slide is a cutting edge which engages a foot plate that is located at the distal end of the stationary shaft. The cutting edge on the cutting slide and the foot plate on the stationary shaft are commonly referred to as the "cutting jaws". When a Kerrison rongeur is in use, the surgeon places the bone to be cut, such as the leading edge of the lamina of a vertebrae, within the cutting jaws. The surgeon then squeezes the handle of the rongeur which causes the cutting edge of the cutting slide to be advanced through that portion of bone to reach the foot plate and thereby amputating that portion of bone.

During use of a Kerrison rongeur, blood, tissue and bone can accumulate between the stationary shaft and cutting slide. Since the accumulated materials are often difficult to remove, subsequent uses of an improperly cleaned rongeur can result in cross-contamination events. For this reason, attempts have been made to design a Kerrison rongeur that can be quickly and easily, fully or partially disassembled to provide access to the spaces between the stationary shaft and cutting slide where the accumulated materials reside.

U.S. Pat. No. 6,126,674 to Janzen describes a Kerrison rongeur that can be completely disassembled by means of a pin that can slide out over a slot in a trigger thereby releasing the slide. A drawback of the device is that the parts can become lost during cleaning and sterilization. U.S. Pat. No. 6,723,103 to Edwards describes a Kerrison rongeur that when held in a retracted position by means of an elastic member, a gap is formed between the cutting slide and the stationary shaft to provide access there between. However, this gap is not sufficiently wide to allow unfettered access between the slide and shaft by brushes for thorough cleaning. Further, the distal portions of the cutting side and stationary shaft remain in contact where the accumulated materials cannot be easily cleaned out. U.S. Pat. No. 5,961,531 to Weber and German Patent Application No. DE102009006689 to Heinemann each describe a convertible rongeur that opens up in an alligator-jaw-like manner which exposes the surfaces between the cutting slide and the stationary shaft. Although the converted devices remain assembled in a single piece since the cutting slides are left dangling in an open position, the devices tend to occupy more space in the sterilization chamber than they do in the closed position and increase the likelihood of the cutting slide becoming bent or otherwise damaged.

SUMMARY OF THE INVENTION

The present invention is directed to a convertible Kerrison rongeur that can be partially disassembled for exposing the sliding surfaces of the rongeur for thorough cleaning while remaining compact and as a single piece. This is accomplished by providing the rongeur with a hinging element having a pivot axis that extends parallel to the functional length of the rongeur. Such an arrangement allows a top cutting slide of the rongeur to flip between an open position where the cutting slide is located off to one side of the rongeur and a closed position.

According to one aspect of the invention, there is provided a rongeur including a shaft member having a length that terminates in a foot plate, a cutting slide slideably coupled with the shaft member and terminating in a cutting edge and means for slidably moving the cutting slide longitudinally relative to the shaft member. To slide cutting slide relative to the shaft member, the cutting slide is provided with a pair of tracking arms arranged about a distal end of cutting slide and a third tracking arm arranged about the proximal end of the cutting slide. These tracking arms are slidably and detachably received within corresponding tracking slots in the shaft member. A hinge assembly is positioned between the cutting slide and the shaft member that has a pivot axis that extends substantially parallel to the length of the shaft member. By combining the sliding and pivoting functions, the cutting slide is allowed to slide longitudinally with respect to the shaft member, and when desired, the tracking arms disengaged from the tracking slots and the cutting slide pivoted off to the side of the shaft to expose the inner, sliding surfaces of the cutting slide and the shaft member for cleaning and repairs.

According to another aspect of the invention there is provided a surgical rongeur including a bottom shaft having a length terminating in a foot plate, a top shaft slidably coupled to the bottom shaft and terminating in a cutting edge, a breach formed between the cutting edge and the foot plate, a handle assembly configured for selectively sliding the top shaft along the bottom shaft, and a pivot axis extending substantially parallel to the length of the bottom shaft. The pivot axis runs through a pin that is fixed to the bottom shaft and slideably and rotatably received by the top shaft. This allows the top shaft to rotate about the pin thereby exposing the inner sliding surfaces of the bottom shaft and the top shaft. In one embodiment, the pin extends through an opening in a sliding member of the top shaft that is slidably received within a gap in the bottom shaft. The opening is elongated radially relative to the pivot axis thus allowing the top shaft to shift radially upward and away from the bottom shaft which is required for disengaging the top shaft from the bottom shaft before rotating the top shaft about the pin.

According to yet another aspect of the invention, there is provided a surgical rongeur including a bottom shaft having a foot plate, a top shaft having a cutting edge, a breach extending between the cutting edge and the foot plate for receiving a human tissue to be cut, a tracking assembly for slidably coupling the bottom shaft with the top shaft, the tracking assembly including at least one tracking arm and at least one tracking slot and a pivot assembly for pivotably coupling the bottom shaft with the top shaft, the pivot assembly having a pivot axis that extends substantially parallel to a length of the bottom shaft. The pivot assembly and the tracking assembly are arranged to selectively transform the rongeur between an open position and a closed position. When the rongeur is in the closed position, the at least one tracking arm is slidably engaged with the at least one tracking slot and the rongeur in ready for use. When the rongeur is in the open position, the at least one tracking arm is disengaged from the at least one tracking slot and the top shaft to rotated about the pivot axis to expose the inner sliding surfaces of the top and bottom shafts.

DETAILED DESCRIPTION OF PRESENTLY PREFERRED EMBODIMENTS

Figure 1:
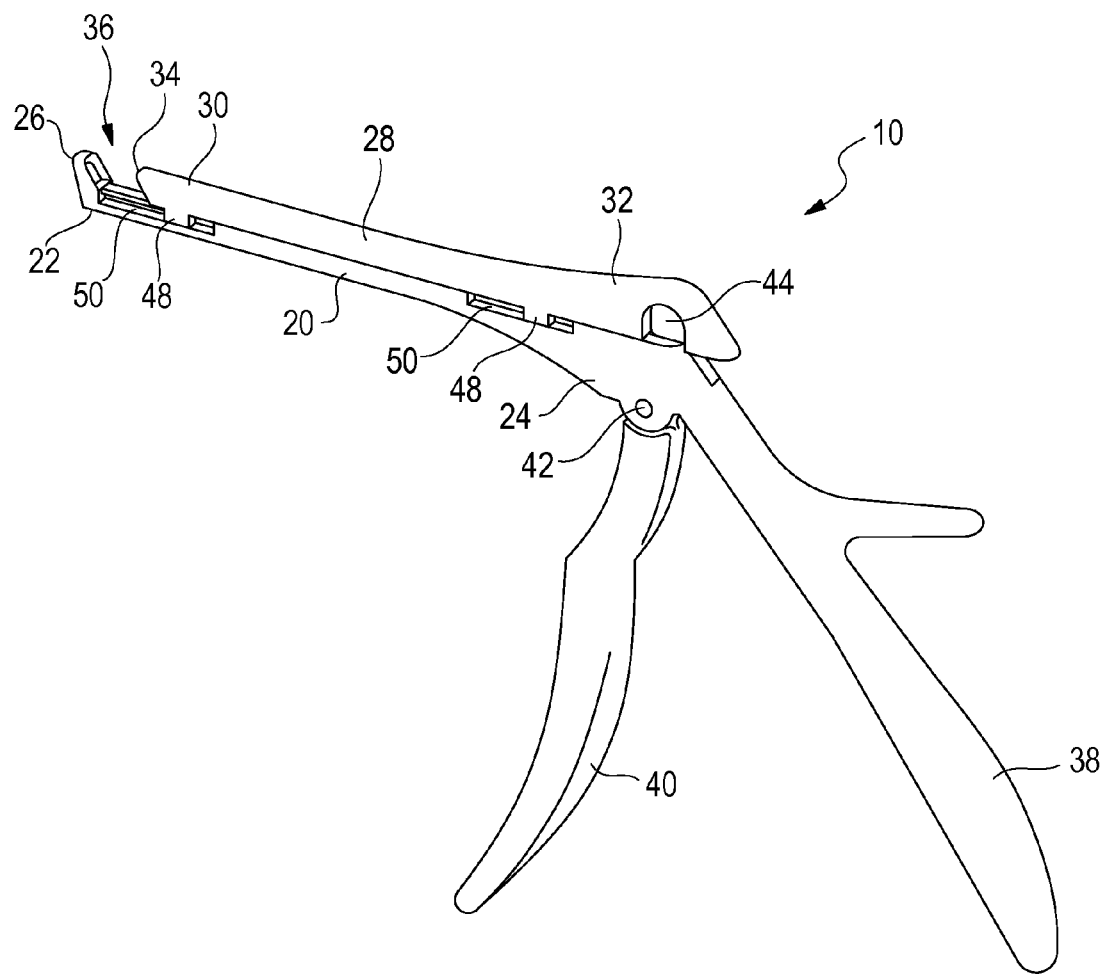
FIG. 1 is perspective view of a rongeur in accordance with a preferred embodiment of the present invention.

FIGS. 1 through 8 illustrate a surgical rongeur 10 in accordance with a preferred embodiment of the present invention. A rongeur 12 in accordance with another preferred embodiment of the present invention is illustrated in FIGS. 9 through 14, where like features share like numbering with FIGS. 1 through 8. Each of rongeurs 10 and 12 generally includes a stationary shaft 20 having a distal end 22, a proximal end 24 and a foot plate 26. A cutting slide 28 having a distal end 30 and a proximal end 32 is slidably coupled with and partially detachable from a top side of shaft 20. Distal end 30 of cutting slide 28 terminates in a cutting edge 34 that together with foot plate 26 defines a breach 36 for receiving bone or other tissue to be cutt.

Figure 5:
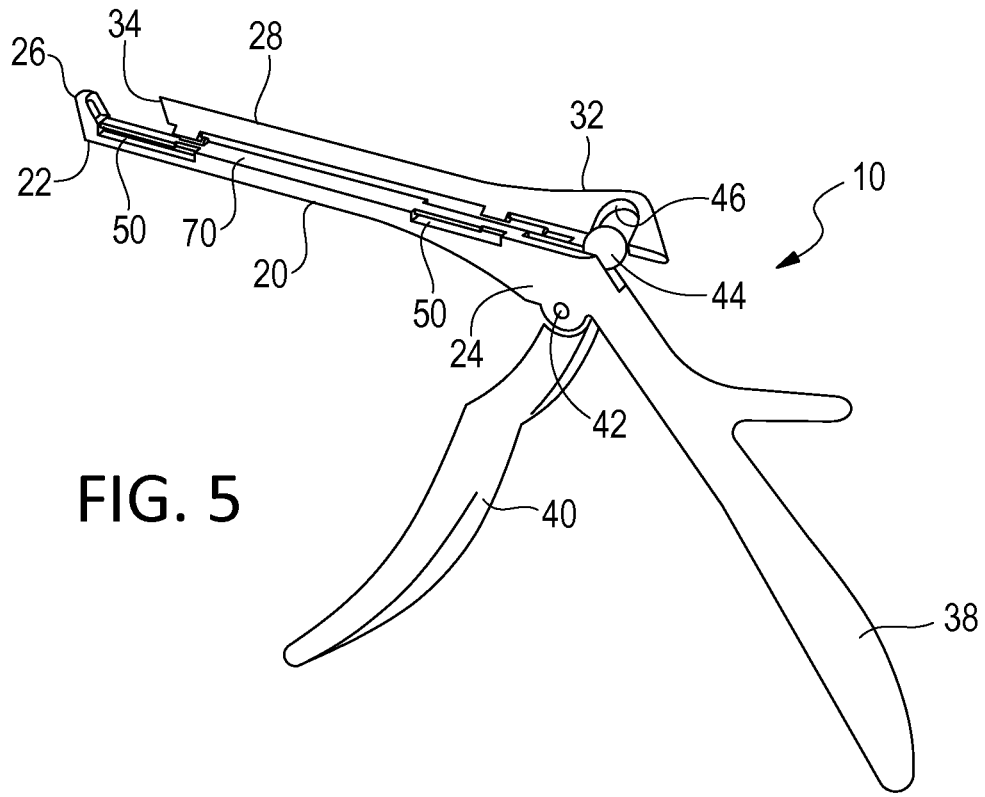
FIG. 5 is a perspective view of the rongeur of FIG. 1 illustrating the disengagement of the tracking arms from the corresponding tracking slots and pivoting of the cutting slide.
Figure 6:
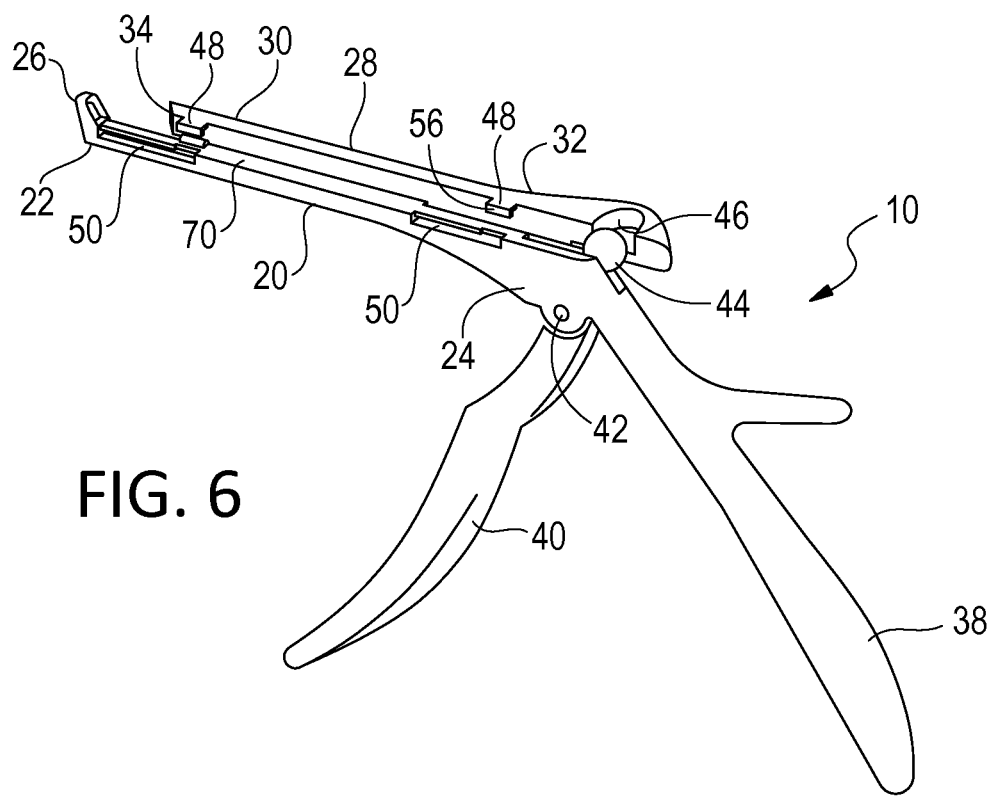
FIG. 6 is a perspective view of the rongeur of FIG. 1 illustrating further pivoting of the cutting slide.

To cut tissue received within breach 36, cutting edge 34 is pressed against foot plate 26 by compressing a handle assembly including a stationary first handle 38 that is integral with proximal end 32 of cutting slide 28 and a second handle 40 that is pivotably coupled to first handle 38 at point 42. At the top of second handle 40 is a head 44 that is received within an open notch 46 (only in rongeur 10) in proximal end 32 of cutting slide 28. As best illustrated in FIG. 5, when the handle assembly is compressed, second handle 40 is pivoted proximally toward first handle 38 causing head 44 to pivot distally toward foot plate 26, in turn causing cutting slide 28 to slide distally until cutting edge 34 engages foot plate 26.

Like prior art rongeurs, when each of rongeurs 10 and 12 is used in surgical procedures, blood, bone and other tissue can accumulate between shaft 20 and cutting slide 28. As described below in further detail, to facilitate cleaning between shaft 20 and cuttings slide 28, each of rongeurs 10 and 20 is configured to partially detach cutting slide 28 from shaft 20 and pivot cutting slide 28 off to a lateral side of shaft 20. This is accomplished by providing each of rongeurs 10 and 12 with a hinge assembly having a pivot axis that extends substantially parallel with the functional lengths of cutting slide 28 and shaft 20 and a tracking assembly that enables sliding shaft 10 to remain slidably coupled to shaft 20 during cutting operations and partially de-coupled from shaft 20 when cleaning is required.

Referring to FIG. 1, there is shown rongeur 10 in a neutral position. In the neutral position, handle 40 is held in place by a spring mechanism (not shown) with handle 40 being neither depressed nor extended. In this position, the tracking assembly is arranged to maintain cutting slide 28 fully engaged with shaft 20 by slidably seating a plurality of L-shaped tracking arms 48, which extend downwardly from cutting slide 28, within corresponding L-shape tracking slots 50 formed within shaft 20. This arrangement prevents any substantial lateral or vertical movement between cutting slide 28 and shaft 20.

Figure 2:
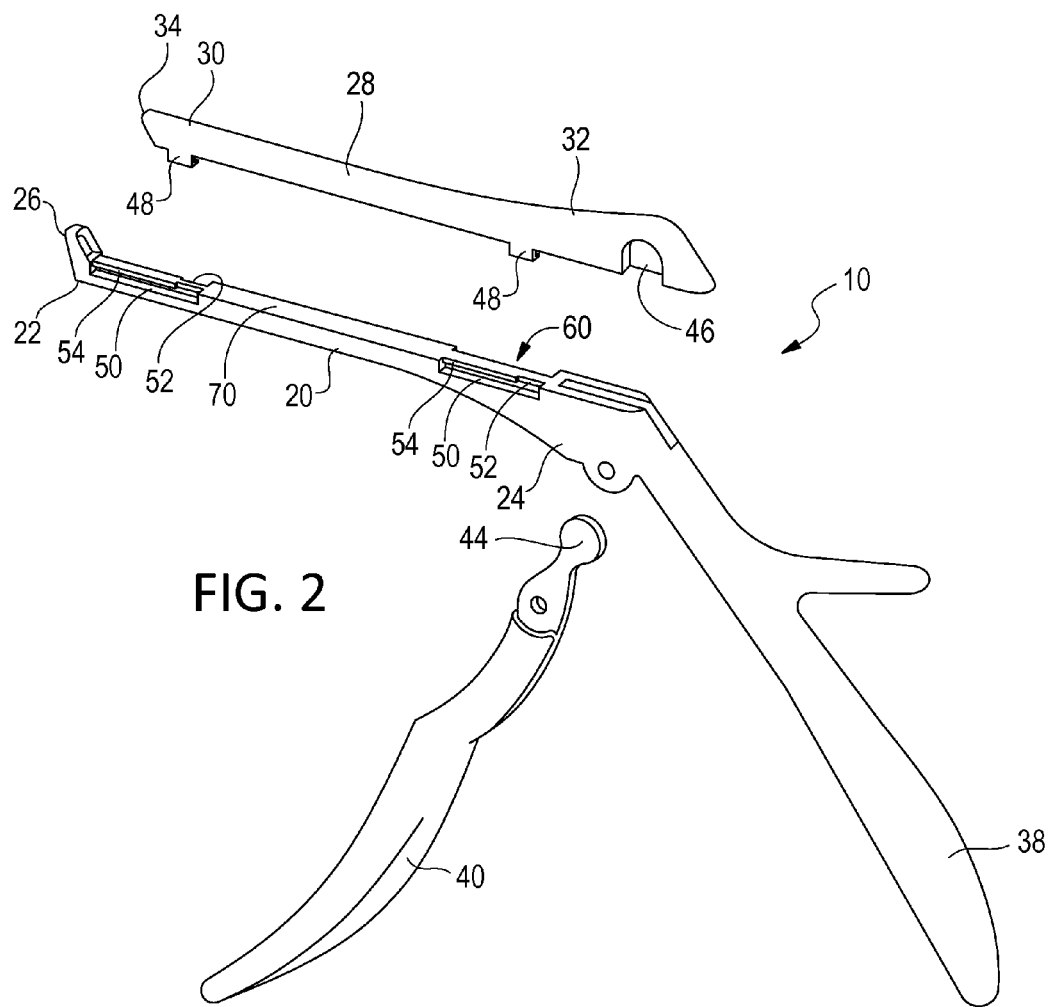
FIG. 2 is an exploded view of the rongeur of FIG. 1.
Figure 7:
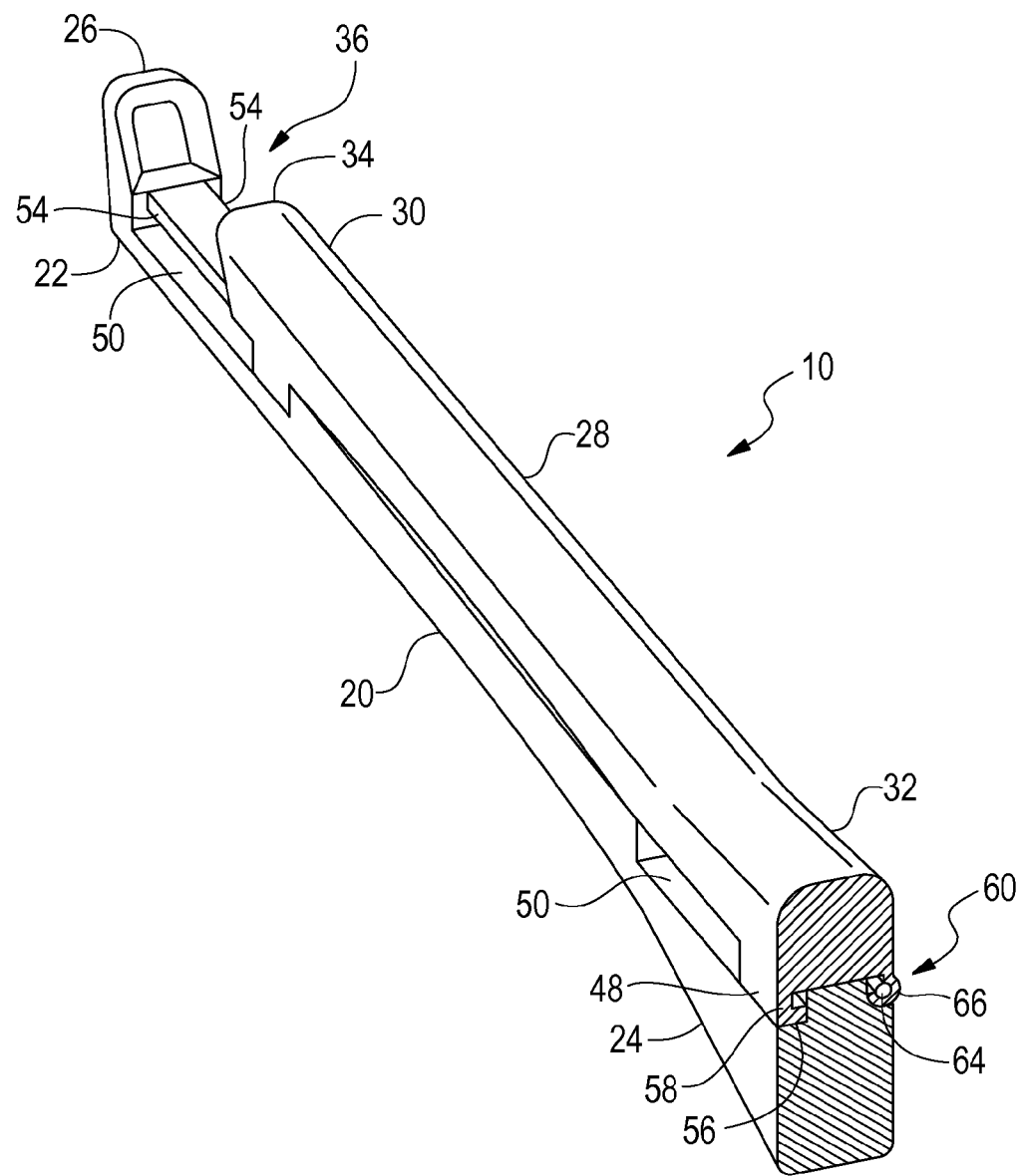
FIG. 7 is a sectional view of the rongeur of FIG. 1 illustrating a closed position.
Figure 8:
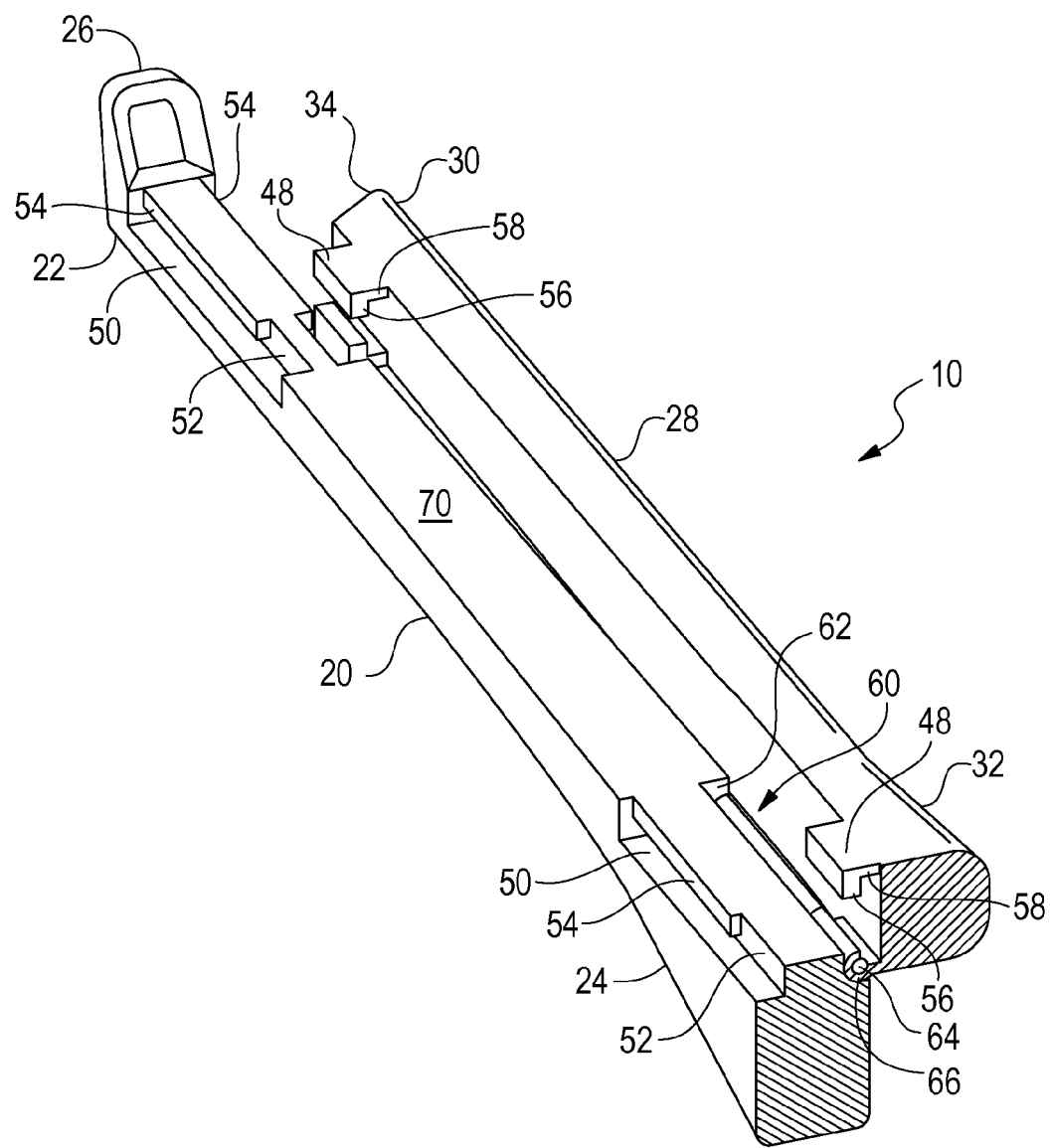
FIG. 8 is a sectional view of the rongeur of FIG. 1 illustrating an open position.
Figure 9:
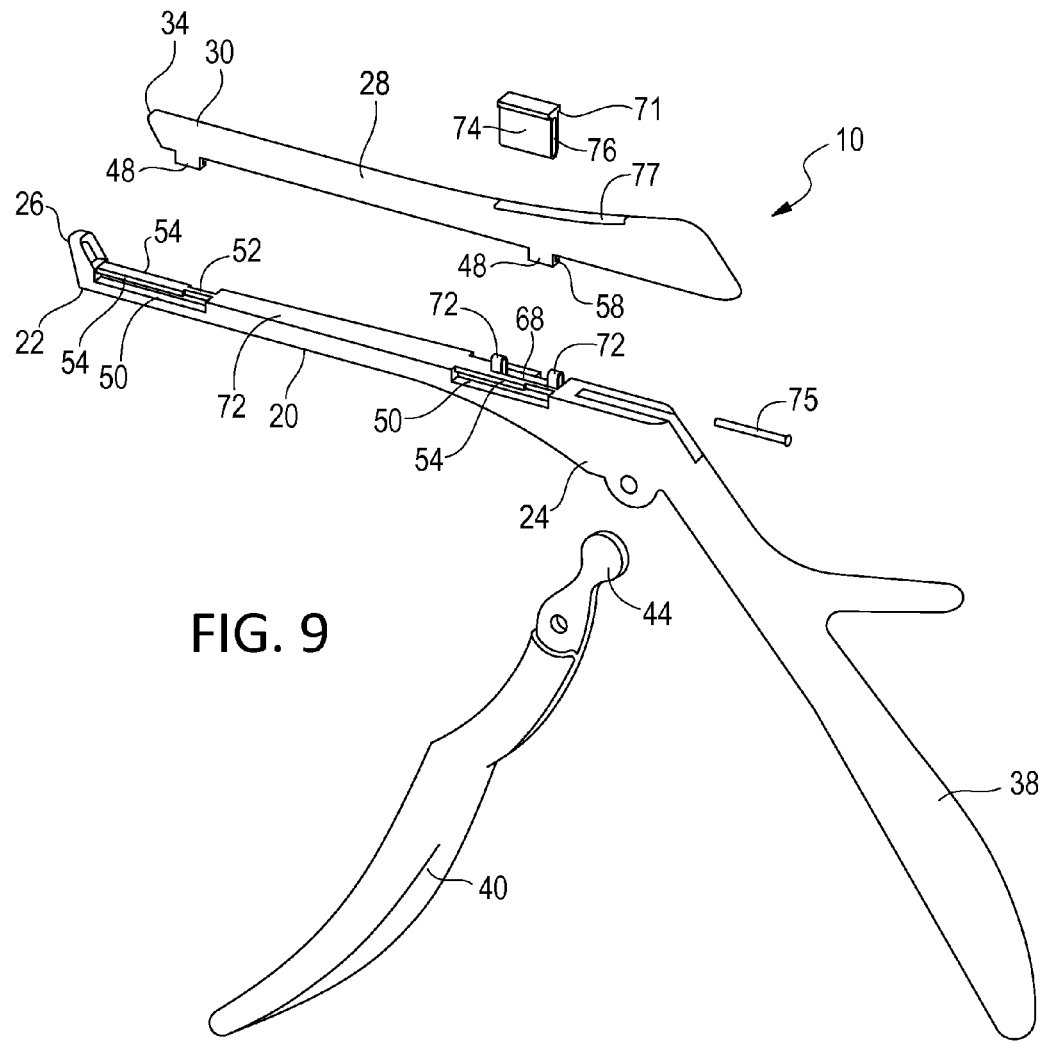
FIG. 9 is an exploded view of a rongeur in accordance with another preferred embodiment of the present invention.
Figure 10:
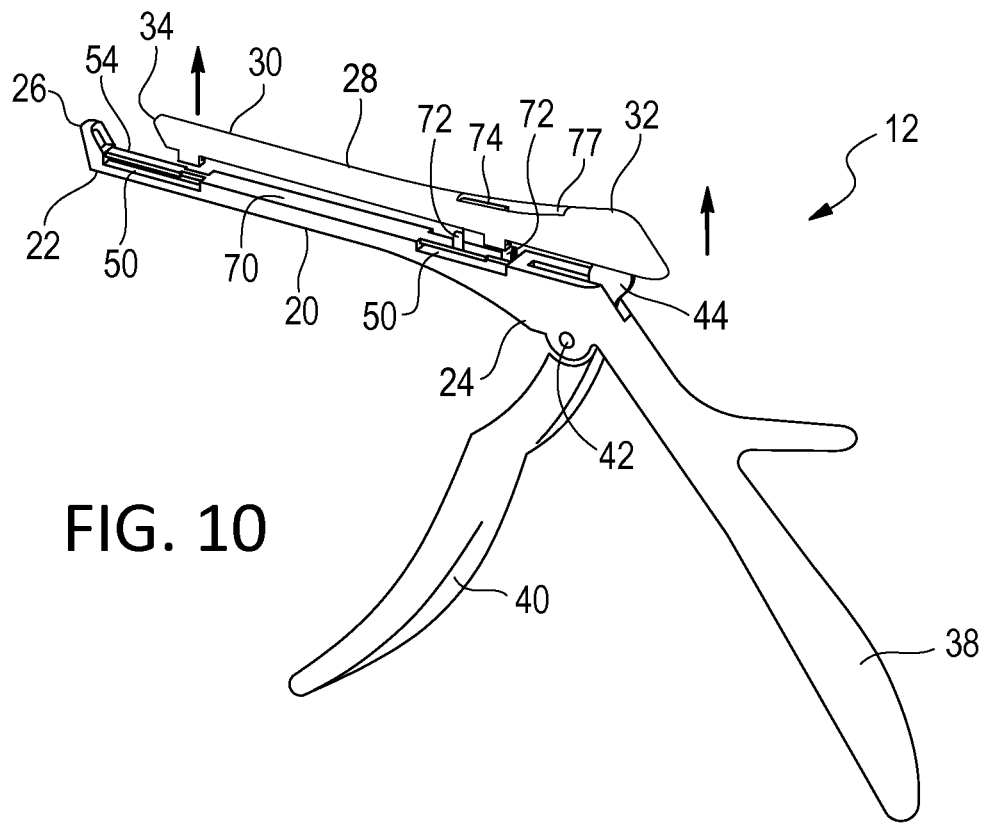
FIG. 10 is a perspective view of the rongeur of FIG. 9 illustrating the disengagement of tracking arms of the cutting slide from corresponding tracking slots of the stationary shaft.
Figure 11:
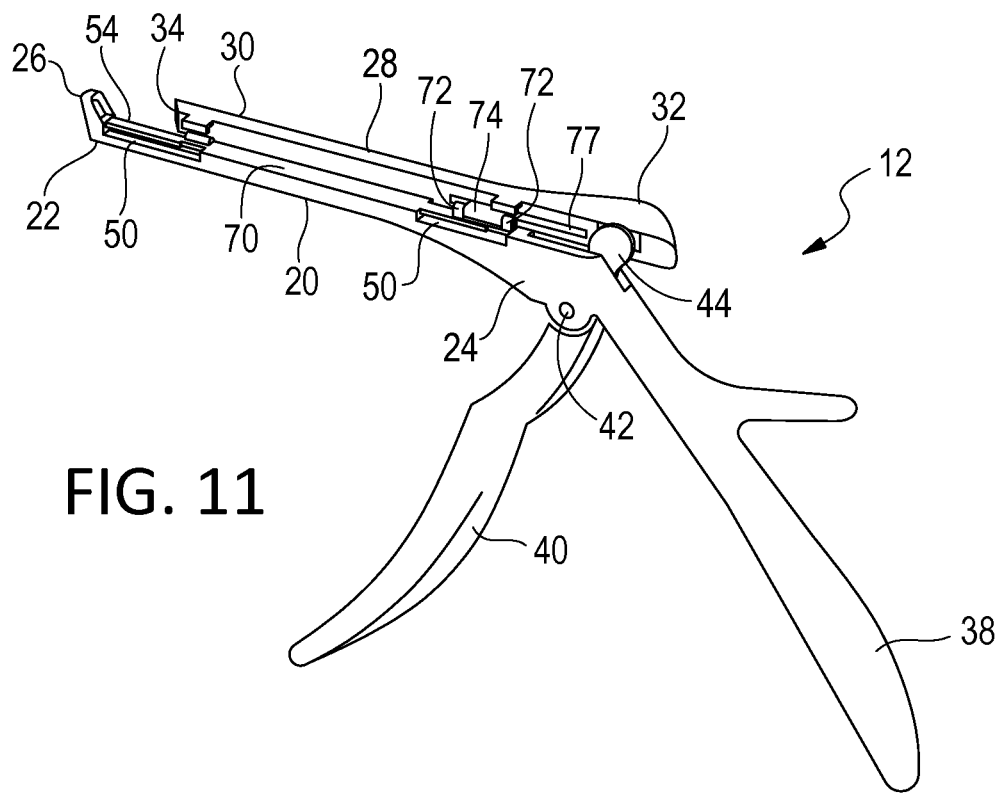
FIG. 11 is a perspective view of the rongeur of FIG. 9 illustrating pivoting of the cutting slide.
Figure 12:
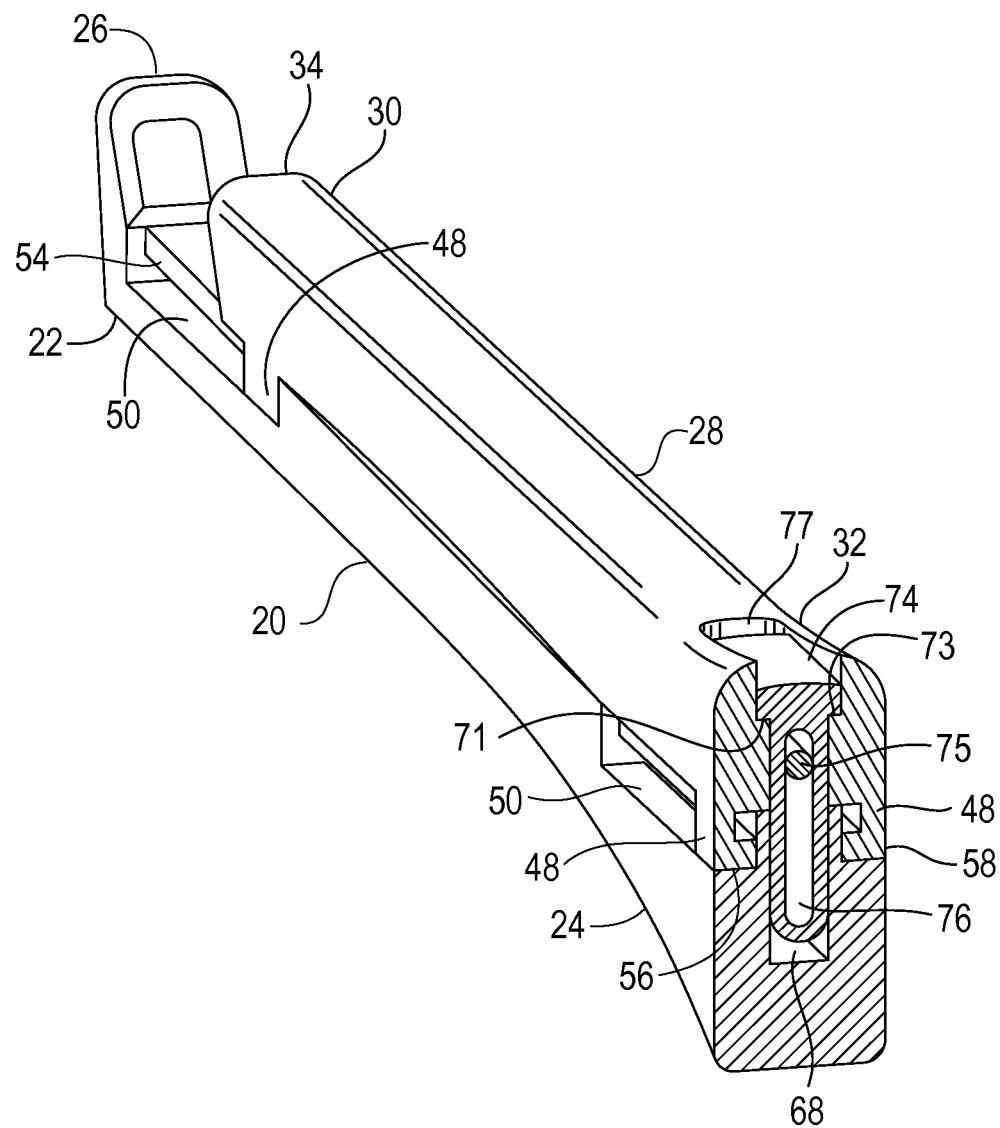
FIG. 12 is a sectional view through a pivot assembly of the rongeur of FIG. 9 illustrating a closed position.

More particularly, referring to FIGS. 2, 7 and 8, the tracking assembly of rongeur 12 includes a pair of opposing tracking slots 50 that are formed in distal end 22 on the lateral sides of shaft 20 immediately proximal to foot plate 22. A third tracking slot 50 is formed within proximal end 24 of shaft 20 on a lateral side thereof opposite the hinge assembly. Each tracking slot 50 extends longitudinally along shaft 10 and is open to a lateral side of shaft 10. Each slot 50 has a smooth lower surface, vertically extending end walls defining the length of slot 50 and an interior wall 52 extending vertically from the lower surface and longitudinally between the end walls. Atop each slot 50 and supported by interior wall 52 is an overhang 54. Each overhang 54 extends laterally from the interior wall 52 above the lower surface of slot 50 but stops short of extending to the plane formed by a lateral side of shaft 20. This creates an L-shaped space having a vertical portion that is that defined between the exposed edge and upper surface of overhang 54 and the plane formed by the lateral side of shaft 20 and a horizontal portion defined by a lower surface of overhang 54, the lower surface of slot 50, interior wall 52 and the plane formed by the exposed edge of overhang 54. The L-shaped space of each slot 50 is configured for receiving a respective L-shaped tracking arm 38 of cutting slide 28 with a horizontal portion 56 of the tracking arm 38 being slidably engaged with the lower surface and interior wall 52 of the slot 50 and the lower surface of overhang 54 and a vertical portion 58 of the tracking arm 38 being slideably engaged with the exposed lateral edge of overhang 54. Arranged in this manner, each tracking arm 48 is locked within a respective tracking slot 50 and allowed to slide longitudinally along shaft 20.

Figure 3:
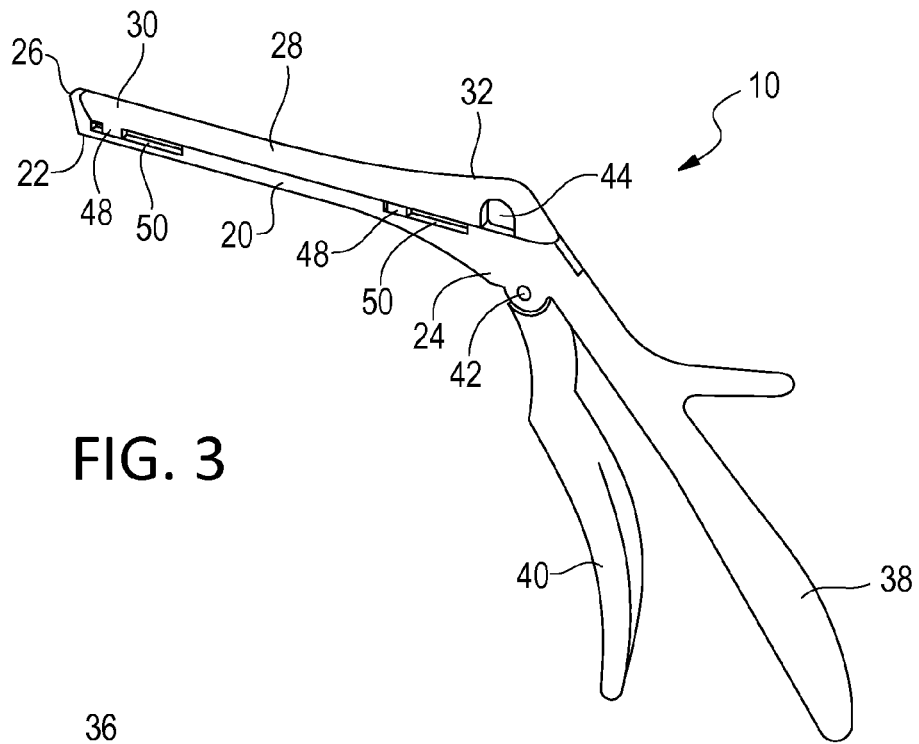
FIG. 3 is a perspective view of the rongeur of FIG. 1 illustrating a cutting edge of the cutting slide engaged with a foot plate of the stationary shaft.
Figure 4:
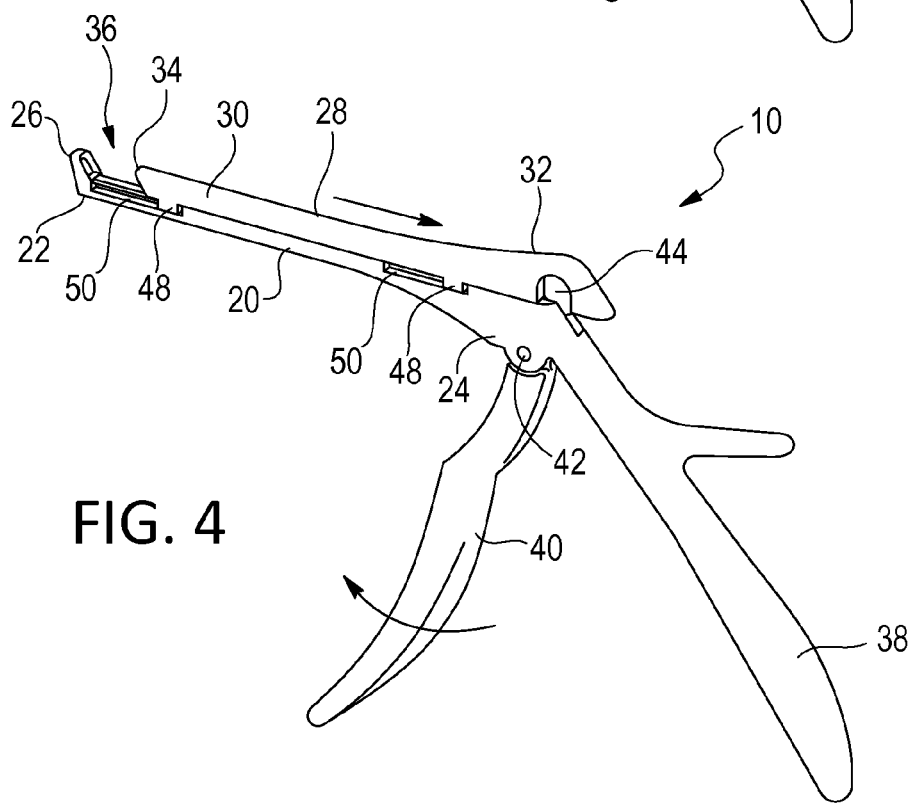
FIG. 4 is a perspective view of the rongeur of FIG. 1 illustrating the alignment of tracking arms of the cutting slide with disengaging sections of corresponding tracking slots of the stationary shaft.

Referring to FIG. 3, by depressing second handle 40, which is biased against a spring member (not shown), cutting slide 28 is slid distally along shaft 20 until cutting edge 34 engages foot plate 26 of shaft 20. When this occurs, each tracking arm 48 is slid distally within a respective tracking slot 50. The interaction of the L-shaped tracking slots 50 with the L-shaped tracking arms 48 thereby allows only longitudinal movement of cutting slide 28 relative to shaft 20. No pivoting or vertical movement between shaft 20 and cutting slide 28 is allowed. Following cutting, second handle 40 is decompressed and rongeur 10 returns to the neutral position depicted in FIG. 1 with each tracking arm 48 being locked within a respective tracking slot 50.

When rongeur 10 requires cleaning it is necessary to gain access to the spaces formed between cutting slide 28 and shaft 28 where blood and tissue tend to accumulate. This is accomplished by first positioning tracking arms 48 within tracking slots 50 in a manner that allows tracking arms 48 to be disengaged from tracking slots 50. Referring to FIGS. 4 through 8, to disengage tracking arms 48 from tracking slots 50, second handle 40 to pivoted distally thereby sliding cutting slide 28 proximally until each tracking arm 48 contacts the proximal end wall of its respective tracking slot 50. In this position, horizontal portion 56 of each tracking arm 48 can be lifted or pivoted vertically out of its respective tracking slot 50 since overhang 54 extends longitudinally from the distal end wall of each slot 50 end wall but stops short of contacting the proximal end wall. This creates a space between the proximal edge of overhang 54 and the proximal end wall of each slot 50 through which a respective tracking arm 48 can be removed vertically from its tracking slot 50.

Upon removal of tracking arms 48 from tracking slot 50, cutting slide 28 is pivoted along a horizontal axis defined by the hinge assembly off to a lateral side of rongeur 10 away from the tracking slot 50 in proximal end 24 of shaft 20. Further, head 44 of second handle 40 is removed from open notch 46. The hinge assembly is positioned within an open gap 60 in a lateral side of shaft 20 opposite to tracking slot 50 located in proximal end 24 of shaft 20. Gap 60 includes a distal end wall 62, a proximal end wall and a pin 64 extending therebetween and in parallel to a length of shaft 20. Pin 64 defines the axis about which cutting slide 28 pivots. Cutting slide 28 is coupled to pin 64 by a cylindrical barrel 66 that extends downwardly from a lower surface of cutting shaft 28. Barrel 66 has an inner circumference large enough to allow barrel 66 to rotate about pin 64 when it is desired to partially disengage cutting slide 28 from shaft 20 and slide longitudinally along pin 64 when rongeur 10 is in use. In this manner, the hinge assembly allows both pivoting and sliding of cutting slide 28 relative to shaft 20.

Rongeur 12 is depicted in FIGS. 9 through 14. Rongeur 12 includes a hinge assembly having a pivot axis that extends parallel to the length and along a central axis of shaft 20. To accommodate a pivot axis along the central axis of shaft 20, shaft 20 includes an open cavity 68 formed in an inner surface 70 of shaft 20 along the central axis thereof within interior wall 52 between tracking slots 50. Extending upwardly from inner surface 70 is a pair of loops 72 with one loop located immediately adjacent to the distal end of cavity 68 and another loop located immediately adjacent to the proximal end of cavity 68. Loops 72 are arranged to receive there between a T-shaped sliding member 74 having an elongate opening 76 aligned with loops 72. T-shaped sliding member 74 is slidably supported by cutting slide which includes a T-shaped slot 77 for inserting T-shape sliding member 74 through cutting slide 28 and into cavity 68. Sliding member 74 is received within cavity 68 and held in place between loops 72 by a locking pin 75 that is inserted through loop 72 on the proximal end of cavity 68, through elongate opening 76 in sliding member 74 and finally through loop 72 in the distal end of cavity 68.

In use, when second handle 40 is compressed, cutting slide 28 slides along shaft 20 toward foot plate 26. During the movement of cutting slide 28, T-shaped sliding member 74 remains stationary while T-shaped slot 77 slides along sliding member 74. To allow for a sufficient sliding distance for cutting slide 28, T-shaped slot 77 has a length that is as least as long as the length of breach 36.

When it is desired to clean rongeur 12, like rongeur 10, it is necessary to disengage tracking arms 48 from tracking slots 50 of the tracking assembly. The tracking assembly of rongeur 12 includes two pairs of corresponding tracking slots 50 and tracking arms 48 combinations, with a first pair being positioned about distal ends 22 and 30, as described above for rongeur 10, and a second pair being positioned about proximal ends 24 and 32. To disengage tracking arms 48 from their corresponding tracking slots 50, second handle 40 is pivoted distally thereby causing cutting slide 28 to slide proximally until tracking arms 48 contact the proximal end walls of tracking slots 50. In this arrangement, cutting slide 28 can be lifted vertically away from shaft 20 with the tracking arms being raised above inner surface 70 of shaft 20.

Figure 13:
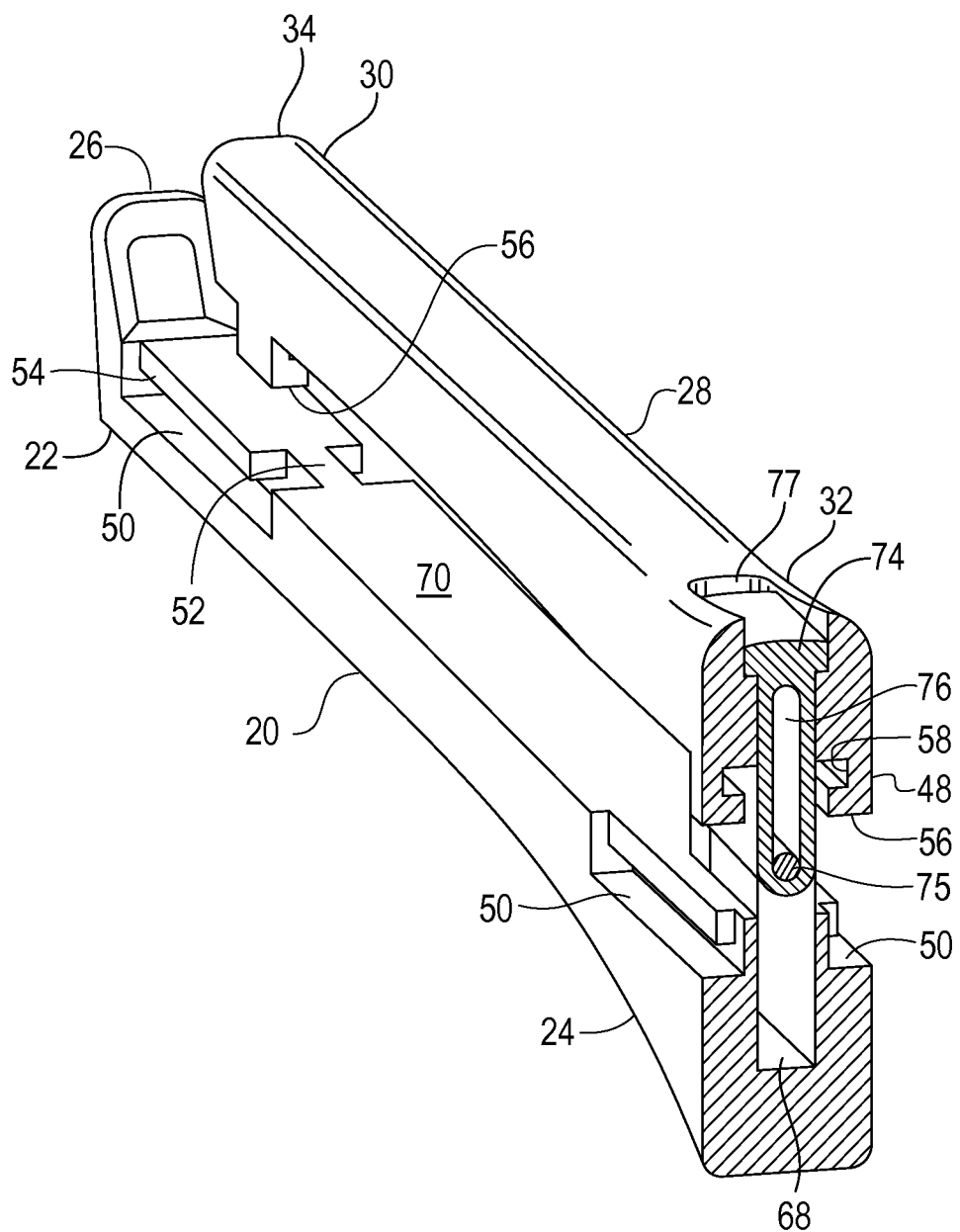
FIG. 13 is a sectional view of the rongeur of FIG. 14.
Figure 14:
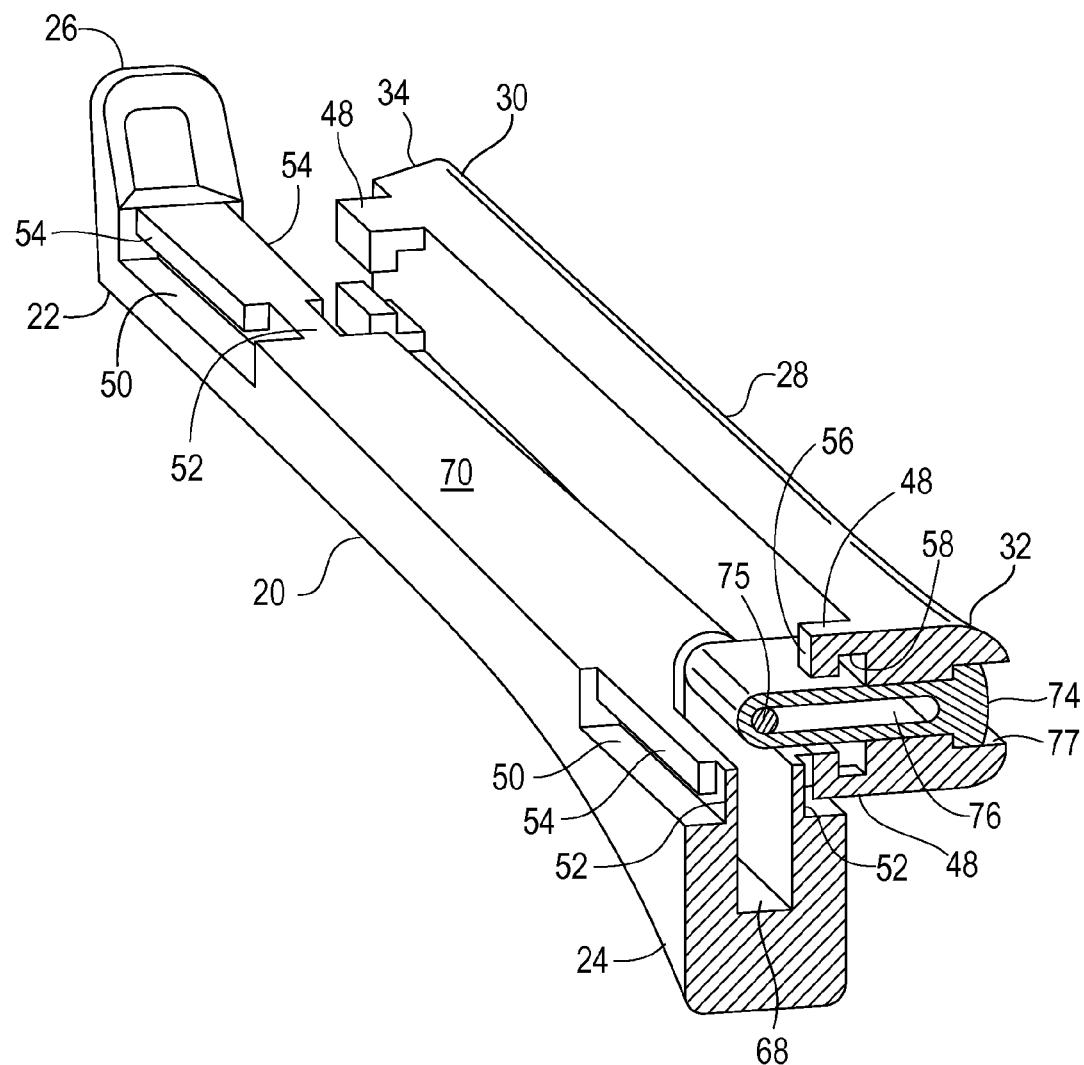
FIG. 14 is a sectional view of the rongeur of FIG. 9 illustrating an open position.

Referring to FIGS. 13 and 14, as cutting slide 70 is lifted vertically, sliding member 74 is lifted vertically by virtue of the interaction of a ledge 71 formed by the horizontal portion of T-shaped cutting slide 74 with a corresponding ledge 73 formed by the horizontal portion of T-shaped slot 77. As this occurs, sliding member 74 is removed from cavity 68 with the upward movement of cutting slide 28, the upward movement being limited by the interaction of pin 75 with the bottom most portion of elongate opening 76. Once the upward movement is stopped, sliding member 74 and cutting slide 28 can be pivoted about pin 75 either clockwise or counter-clockwise to expose inner surface 70 and the lower surface of cutting slide 28 to cleaning and repair.

As will be apparent to one skilled in the art, various modifications can be made within the scope of the aforesaid description. Such modifications being within the ability of one skilled in the art form a part of the present invention and are embraced by the claims below.

The invention claimed is:

1. A surgical rongeur comprising,
a shaft member having a length, a proximal end and a distal end, the distal end of the shaft member including a foot plate,
a cutting slide slideably coupled with the shaft member, the cutting slide having a proximal end and a distal end, the distal end of the cutting slide including a cutting edge that is selectively engagable with the foot plate, and
means to slidably move the cutting slide longitudinally relative to the shaft member,
wherein the cutting slide is pivotably coupled with the shaft member by a hinge assembly forming a pivot axis that extends longitudinally relative to the length of the shaft member and wherein the hinge assembly is located at least partially within a gap arranged along a centerline of the of the shaft member.

2. The surgical rongeur according to claim 1 wherein the cutting slide includes at least one tracking arm slidably received within at least one tracking slot in the shaft member, the at least one tracking slot having a tracking arm disengaging portion configured for releasing the tracking arm from within the tracking slot.

3. The surgical rongeur according to claim 2 wherein the tracking arm disengaging portion is arranged at a proximal end of the tracking slot.

4. The surgical rongeur according to claim 3 wherein the at least one tracking arm includes a pair of opposed tracking arms arranged about the distal end of cutting slide and a third tracking arm arranged about the proximal end of the cutting slide and the at least one tracking slot includes a pair of opposed tracking slots arranged about the distal end of shaft member and a third tracking slot arranged about the proximal end of the shaft member.

5. A method for partially disassembling the surgical rongeur of claim 2 comprising disengaging the at least one tracking arm from the at least one tracking slot and rotating the cutting slide at least partially about the pivot axis.

6. The surgical rongeur according to claim 1 wherein the hinge assembly includes a pin fixed to the shaft member that is rotatably and slidably received within a barrel fixed to the cutting slide.

7. The surgical rongeur according to claim 6 wherein the pin is received within a slot arranged along a lateral side of the rongeur.

8. The surgical rongeur according to claim 1 further comprising a tracking slot having a disengaging portion configured for releasing a tracking arm from within the tracking slot, the tracking slot being arranged along a first lateral side of the rongeur and the hinge assembly being arranged along a second lateral side of the rongeur.

9. The surgical rongeur according to claim 1 wherein the hinge assembly includes a pin fixed to the shaft member and a pin receiving member, the pin being slidably and rotatably received within the pin receiving member and the pin receiving member being slidably received within a gap.

10. The surgical rongeur according to claim 1 wherein the means for slidably moving the cutting slide includes a first handle leg pivotably coupled to a second handle leg.

11. A surgical rongeur comprising,
a bottom shaft having a length terminating in a foot plate,
a top shaft slidably coupled to the bottom shaft and terminating in a cutting edge,
a breach formed between the cutting edge and the foot plate,
a handle assembly configured for selectively sliding the top shaft along the bottom shaft and engaging the cutting edge with the foot plate, and
a pivot axis extending longitudinally relative to the length of the bottom shaft, the top shaft being both rotatable about the pivot axis and slidable longitudinally relative to the pivot axis.

12. The surgical rongeur according to claim 11 wherein the pivot axis extends axially through a pin that is slideably and rotatably received by the top shaft.

13. The surgical rongeur according to claim 11 wherein the pivot axis extends through a slot arranged along a lateral side of the rongeur.

14. The surgical rongeur according to claim 11 wherein the pivot axis extends through an opening in a sliding member of the top shaft, the sliding member being slidably received within a gap in the bottom shaft.

15. The surgical rongeur according to claim 11 wherein the top shaft includes a pair of tracking arms arranged about a distal end of the top shaft and a third tracking arm arranged about the proximal end of the top shaft and the bottom shaft includes a pair of tracking slots arranged about the distal end of bottom shaft and a third tracking slot arranged about the proximal end of the bottom shaft, the pair of tracking arms being slidably received within the pair of tracking slots and the third tracking arm being slidably received within the third tracking slot.

16. A method for partially disassembling the surgical rongeur of claim 11 comprising rotating the top shaft at least partially about the pivot axis.

17. A surgical rongeur comprising,
a bottom shaft having a length terminating in a foot plate,
a top shaft slidably coupled to the bottom shaft and terminating in a cutting edge,
a breach formed between the cutting edge and the foot plate,
a handle assembly configured for selectively sliding the top shaft along the bottom shaft and engaging the cutting edge with the foot plate, and
a pivot axis extending longitudinally relative to the length of the bottom shaft about which the top shaft is configured to rotate,
wherein the pivot axis extends axially through a pin that is slideably and rotatably received by the top shaft and the pin has a length that allows the top shaft to slide a distance along the pin, the distance being sufficiently long to allow a tracking arm and a tracking slot of the rongeur to disengage thereby permitting the top shaft to pivot about the pivot axis.

18. A surgical rongeur comprising,
a bottom shaft having a length terminating in a foot plate,
a top shaft slidably coupled to the bottom shaft and terminating in a cutting edge,
a breach formed between the cutting edge and the foot plate,
a handle assembly configured for selectively sliding the top shaft along the bottom shaft and engaging the cutting edge with the foot plate, and
a pivot axis extending longitudinally relative to the length of the bottom shaft about which the top shaft is configured to rotate,
wherein the pivot axis extends through a gap arranged essentially along a centerline of the bottom shaft.

19. A surgical rongeur comprising,
a bottom shaft having a length terminating in a foot plate,
a top shaft slidably coupled to the bottom shaft and terminating in a cutting edge,
a breach formed between the cutting edge and the foot plate,
a handle assembly configured for selectively sliding the top shaft along the bottom shaft and engaging the cutting edge with the foot plate, and
a pivot axis extending longitudinally relative to the length of the bottom shaft about which the top shaft is configured to rotate,
wherein the pivot axis extends through an opening in the top shaft, the opening extending a distance radially from the pivot axis that is sufficiently long to allow a tracking arm and a tracking slot of the rongeur to disengage and the top shaft to pivot about the pivot axis in either a clockwise or counter-clockwise direction.

20. A surgical rongeur comprising,
a bottom shaft having a foot plate,
a top shaft having a cutting edge,
a breach extending between the cutting edge and the foot plate for receiving a human tissue to be cut,
a tracking assembly slidably coupling the bottom shaft with the top shaft, and
a pivot axis extending longitudinally relative to a length of the bottom shaft, the top shaft being both rotatable about the pivot axis and slidable longitudinally relative to the pivot axis,
wherein the top shaft is moveable between a closed position for operating the rongeur and an open position for cleaning between the bottom shaft and the top shaft, the open position including the top shaft having a length arranged longitudinally relative to the length of the bottom shaft.

21. The surgical rongeur according to claim 20 wherein, when the rongeur is in the closed position, at least one tracking arm of the tracking assembly is slidably engaged within at least one tracking slot of the tracking assembly, and wherein the rongeur is in the open position, the at least one tracking arm is disengaged from the at least one tracking slot.

22. A method of partially disassembling the surgical rongeur of claim 20 comprising adjusting the rongeur from the closed position to the open position.

* * * * *